United States Patent [19]

Kawai et al.

[11] Patent Number: 5,032,680
[45] Date of Patent: Jul. 16, 1991

[54] 2'-DEOXY-5-FLUOROURIDINE DERIVATIVES

[75] Inventors: Tsutomu Kawai; Fumio Mori, both of Kurashiki; Setsuo Takeda, Tokushima; Hitoshi Saito, Tokushima; Norio Unemi, Tokushima, all of Japan

[73] Assignees: Kuraray Co., Ltd., Okayama; Taiho Pharmaceutical Co., Ltd., Tokyo, both of Japan

[21] Appl. No.: 314,924

[22] Filed: Feb. 24, 1989

[30] Foreign Application Priority Data

Feb. 29, 1988 [JP] Japan .................................. 63-47864

[51] Int. Cl.$^5$ ..................... A01N 43/04; A61K 31/70; C07H 17/02
[52] U.S. Cl. ......................................... 536/23; 536/29; 544/243; 544/311; 544/313
[58] Field of Search ...................... 536/23, 29; 514/50, 514/51; 544/243, 311, 313

[56] References Cited

U.S. PATENT DOCUMENTS

| 4,503,045 | 3/1985 | Fujii | 536/23 |
| 4,599,404 | 7/1986 | Fujii | 536/23 |
| 4,605,645 | 8/1986 | Watanabe | 536/29 |
| 4,684,631 | 8/1987 | Hori | 536/29 |
| 4,740,503 | 4/1988 | Hori | 514/51 |

FOREIGN PATENT DOCUMENTS

| 0081386 | 6/1983 | European Pat. Off. . |
| 58-99499 | 6/1963 | Japan . |
| 128699 | 8/1982 | Japan . |
| 59-70699 | 4/1984 | Japan . |
| 59-93096 | 5/1984 | Japan . |
| 61-91195 | 5/1986 | Japan . |
| 61-91196 | 5/1986 | Japan . |
| 61-152694 | 7/1986 | Japan . |
| 61-236793 | 10/1986 | Japan . |

Primary Examiner—Robert A. Wax
Assistant Examiner—Fred Tsung
Attorney, Agent, or Firm—Wenderoth, Lind & Ponack

[57] ABSTRACT

2'-Deoxy-5-fluorouridine derivatives of the formula

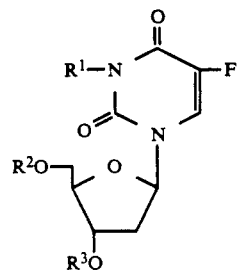

wherein, $R^1$ is hydrogen atom or an acyl group and $R^2$ and $R^3$ are respectively hydrogen atom, an acyl group or a group of the formula

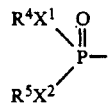

wherein $X^1$ and $X^2$ are respectively oxygen atom or sulfur atom; $R^4$ is a phenyl group, a benzyl group or a naphthyl group each of which may be substituted by an alkyl group, an alkoxyl group, an alkoxycarbonyl group, an alkylthio group, and acyl group, a halogen atom, trifluoromethyl group, nitro group, cyano group, carboxyl group and/or methylenedioxy group and $R^5$ is an alkyl group, an alkenyl group or one of the groups represented by $R^4$ which is the same as or different from $R^4$, at least one of $R^2$ and $R^3$ being a group of the formula

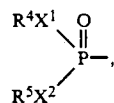

which exhibit excellent antitumour activities and have lower toxicity, methods of the production thereof and antitumour compositions containing said 2'-deoxy-5-fluorouridine derivatives.

7 Claims, No Drawings

2'-DEOXY-5-FLUOROURIDINE DERIVATIVES

FIELD OF THE INVENTION

This invention relates to novel 2'-deoxy-5-fluorouridine derivatives, methods for the production thereof and antitumour compositions containing the same.

DESCRIPTION OF THE PRIOR ART

It has been recognized that 2'-deoxy-5-fluorouridine (hereinafter referred to as FdUrd) displays an extremely potent tumour proliferation-inhibitory action in the cytostatic potency test (in vivo). However, since FdUrd is rapidly metabolized and excreted, and a large portion thereof is decomposed into 5-fluorouracil, FdUrd can not be found to exhibit any particular superior effects as compared with 5-fluorouracil. Besides, the toxicity thereof is strong. Therefore, FdUrd is at present only used as intraarterial injections in USA alone [Physicians' Desk Reference 32 edition, 1387 (1978)]. A lot of studies have been already conducted for the purpose of improving the defects of FdUrd. There have been proposed phosphoric acid amidate derivatives (See the gazette of Japanese Published Unexamined Patent Application (Kokai) No. 128699/1982), phosphoric acid ester derivatives of aliphatic hydrocarbons optionally having ether-bond or imino-bond at 5'-position, and the like (See the gazettes of Tokkai Nos. 99499/1983, 70699/1984, 93096/1984, 91195/1986, 91196/1986, 152694/1986, 236793/1986).

Anticancer activities of any of the above-mentioned various FdUrd derivatives are not fully enhanced as compared with FdUrd, and side-effects thereof are hardly sufficiently reduced.

One of the objects of this invention is to provide novel FdUrd derivatives which have higher anticancer activities and lower toxicities as compared with FdUrd and other FdUrd derivatives hitherto known. Another object of the present invention is to provide methods for the production of such novel FdUrd derivatives. One of the other objects of this invention is to provide antitumour compositions containing said novel FdUrd derivatives as the effective ingredients which can be administered orally and through injection.

SUMMARY OF THE INVENTION

According to the present invention, the above-mentioned objects can be attained by providing (1) 2'-deoxy-5-fluorouridine derivatives of the formula

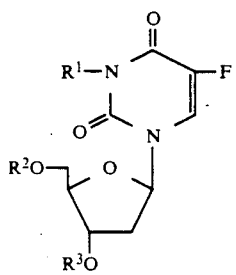
(I)

wehrein $R^1$ is hydrogen atom or an acyl group and $R^2$ and $R^3$ are respectively hydrogen atom, an acyl group or a group of the formula

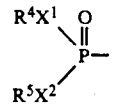

wherein $X^1$ and $X^2$ are respectively oxygen atom, $R^4$ is a phenyl group, a benzyl group, or a naphthyl group each of which may be substituted by an alkyl group, an alkoxyl group, an alkoxycarbonyl group, an alkylthio group, an acyl group, a halogen atom, trifluoromethyl group, nitro group, cyano group, carboxyl group or methylenedioxy group and $R^5$ is an alkyl group, an alkenyl group or one of the groups represented by $R^4$ which is the same as or different from $R^4$, at least one of $R^2$ and $R^3$ being a group of the formula

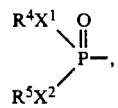

(2) a method for the production of the 2'-deoxy-5-fluorouridine derivatives of the formula (I) which comprises reacting a compound of the formula

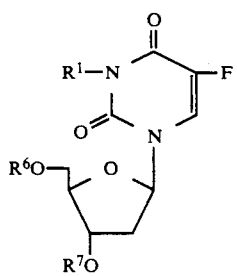
(II)

wherein $R^1$ is as defined above and $R^6$ and $R^7$ are respectively hydrogen atom or a hydroxyl group protecting group, both of $R^6$ and $R^7$ never being a hydroxyl group-protecting group with a compound of the formula

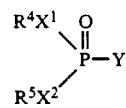
(III)

wherein $X^1$, $X^2$, $R^4$ and $R^5$ are respectively as defined above and Y is a halogen atom, if necessary, followed by the deprotection reaction of the reaction product for the hydroxyl group-protecting group, (3) a method for the production of the 2'-deoxy-5-fluorouridine derivatives of the formula (I) which comprises reacting a compound of the formula (II) with a compound of the formula

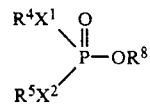
(IV)

wherein $X^1$, $X^2$, $R^4$ and $R^5$ are respectively as defined above and $R^8$ is hydrogen atom, a metal cation, an ammonium ion or an organic ammonium ion in the presence of a condensating agent, if necessary, followed by the deprotection reaction of the reaction product for the hydroxyl group-protecting group and (4) the antitumour compositions which are characterized by ) containing 2'-deoxy-5-fluorouridine derivatives of the formula (I) as the effective ingredients.

DETAILED DESCRIPTION OF THE INVENTION

The definitions of $R^1$, $R^2$ and $R^3$ in the formula (I) are in detail explained below. $R^1$ is hydrogen atom or an acyl group. As the acyl group represented by $R^1$, there are mentioned aliphatic acyl groups having 1 to 7 carbon atoms such as formyl, acetyl, propionyl, butyryl, valeryl and hexanoyl; benzoyl group; 3,4-methylenedioxybenzoyl group; aromatic acyl groups such as benzoyl group or naphthoyl group which have one or at least two substituent(s) such as alkyl groups having 1 to 6 carbon atoms such as methyl, ethyl, n-propyl, isopropyl, n-butyl, isobutyl, t-butyl, n-hexyl and isohexyl; alkoxyl groups having 1 to 6 carbon atoms such as methoxy, ethoxy, n-propoxy, isopropoxy, n-butoxy, isobutoxy, t-butoxy, n hexyloxy and isohexyloxy; halogen atoms such as fluorine, chlorine, bromine and iodine; alkoxycarbonyl groups having 2 to 7 carbon atoms such as methoxycarbonyl, ethoxycarbonyl, n-butoxycarbonyl and n-hexyloxycarbonyl; cyano group and nitro group at the o-, m- or p-position. When the benzoyl or naphthoyl group has at least two substituents, the substituents may be the same or different. As $R^1$, preferred are hydrogen atom, acetyl group, benzoyl group, m- or p-methylbenzoyl, m- or p-methoxybenzoyl, 3,4-methylenedioxybenzoyl and the like. $R^2$ and $R^3$ are respectively hydrogen atom, an acyl group or a group of the formula

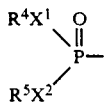

In the formula, $X^1$ and $X^2$ are respectively oxygen atom or sulfur atom. $R^4$ is a phenyl group, a benzyl group or a naphthyl group each of which may have one substituent or at least two substituents such as alkyl groups having 1 to 6 carbon atoms such as methyl, ethyl, n-propyl, isopropyl, n-butyl, isobutyl, t-butyl, n-hexyl and isohexyl; alkoxyl groups having 1 to 6 carbon atoms such as methoxy, ethoxy, n-propoxy, isopropoxy, n-butoxy, isobutoxy, t-butoxy, n-hexyloxy and isohexyloxy; alkoxycarbonyl groups having 2 to 7 carbon atoms such as methoxycarbonyl, n-butoxycarbonyl and n-hexyloxycarbonyl; alkylthio groups having 1 to 6 carbon atoms such as methylthio, ethylthio, n-butylthio, isobutylthio, n-hexylthio and isohexylthio; acyl groups having 1 to 7 carbon atoms such as formyl, acetyl, propionyl, butyryl, valeryl, hexanoyl and benzoyl; halogen atoms such as fluorine, chlorine, bromine and iodine; trifluoromethyl group; nitro group; cyano group; carboxyl group and methylenedioxy group. Herein, the substituent(s) of the phenyl group, the benzyl group and the naphthyl group may attach thereto at any position of the benzene ring and the naphthalene ring. When the phenyl group, the benzyl group or the naphthyl group have at least two substituents, the substituents may be the same or different. As the phenyl group, the benzyl group or the naphthyl group having at least two substituents, there are mentioned 2,3-dichlorophenyl, 2,4-dichlorophenyl, 3,4-dichlorophenyl, 2,6-dichlorophenyl, 3,5-dichlorophenyl, 4-chloro-3-methylphenyl, 2-bromo-4-methylphenyl, 2-chloro-4-nitrophenyl, 3,4-dimethylphenyl, 6-t-butyl-4-methylphenyl, 2,3,5-trichlorophenyl, 2,3,5-trimethylphenyl, 2,4-dichlorobenzyl, 2,5-dichlorobenzyl, 2,6-dichlorobenzyl, 3,4-dichlorobenzyl, 3,5-dichlorobenzyl, 4-chloro-3-nitrobenzyl, 2,4-dimethylbenzyl, 2,4-dichloro-1-naphthyl and the like. $R^5$ includes groups represented by $R^4$ which are the same or different, or alkyl groups or alkenyl groups having 1 to 15 carbon atoms. As the alkyl group, there may be mentioned methyl, ethyl, n-butyl, isobutyl, n-octyl, n-dodecyl, 3-methylbuten-1-yl, 3,7-dimethyloctan-1-yl, and the like. As the alkenyl group, there may be mentioned 2-buten-1-yl, 2-methylbuten-1-yl, 3,7-dimethyl-2,6-octadien-1-yl, 3,7'-dimethyl-6-octen-1-yl and so on. Among others, as $R^4$ and $R^5$, respectively preferred are m- or p-chlorophenyl group, m- or p-fluorophenyl group, m- or p-trifluoromethylphenyl group, 3,4-dichlorophenyl group, 3,5-dichlorophenyl group, 2,4-dichlorophenyl group, 2,3-dichlorophenyl group, m- or p-bromophenyl group, m or p-cyanophenyl group, m- or p-nitrophenyl, m- or p-methoxycarbonylphenyl, m- or p-acetylphenyl group, m- or p-methylphenyl and the like. As the acyl group represented respectively by $R^2$ and $R^3$, there may be mentioned acyl groups represented by $R^1$ as mentioned above. The preferred examples thereof are acetyl, propionyl, butyryl, benzoyl, m-methylbenzoyl and the like.

As concrete examples of the 2'-deoxy-5-fluorouridine derivatives of the formula (I), the following may be mentioned.

Diphenyl 2'-deoxy-5-fluoro-5'-uridylate
Diphenyl 2'-deoxy-5-fluoro-3'-uridylate
Diphenyl 2'-deoxy-5'-O-(diphenoxyphosphinyl)-5-fluoro-3'-uridylate
Diphenyl 3-benzoyl 2'-deoxy-5-fluoro-5'-uridylate
Di-p-methylphenyl 2'-deoxy-5-fluoro-5'-uridylate
Di-p-n-hexylphenyl 2'-deoxy-5-fluoro-5'-uridylate
Di-p-methoxyphenyl 2'-deoxy-5-fluoro-5'-uridylate
Di-m-n-hexyloxyphenyl 2'-deoxy-5-fluoro-5'-uridylate
Di-p-methoxycarbonylphenyl 2'-deoxy-5-fluoro-5'-uridylate
Di-m-methoxycarbonylphenyl 2'-deoxy-5-fluoro-5'-uridylate
Di-p-n-hexyloxycarbonylphenyl 2'-deoxy-5-fluoro-5'-uridylate
Di-p-methylthiophenyl 2'-deoxy-5-fluoro-5'-uridylate
Di-p-n-hexylthiophenyl 2'-deoxy-5-fluoro-5'-uridylate
Di-m-acetylphenyl 2'-deoxy-5-fluoro-5'-uridylate
Di-p-acetylphenyl 2'-deoxy-5-fluoro-5'-uridylate
Di-p-benzoylphenyl 2'-deoxy-5-fluoro-5'-uridylate
Di-m-fluorophenyl 2'-deoxy-5-fluoro-5'-uridylate
Di-p-fluorophenyl 3-p-hexyloxycarbonylbenzoyl-2'-deoxy-5-fluoro-5'-uridylate
Di-p-fluorophenyl 3-p-nitrobenzoyl-2'-deoxy-5-fluoro-5'-uridylate
Di-p-fluorophenyl 2'-deoxy-5-fluoro-5'-uridylate
Di-p-fluorophenyl 3-(3,4-methylenedioxybenzoyl)-2'-deoxy-5-fluoro -5'-uridylate
Di-o-chlorophenyl 2'-deoxy-5-fluoro-5'-uridylate
Di-m-chlorophenyl 2'-deoxy-5-fluoro-5'-uridylate
Di-m-chlorophenyl 3-m-methoxybenzoyl-2'-deoxy-5-fluoro-5'-uridylate
Di-m-chlorophenyl 3-p-methylbenzoyl-2'-deoxy-5-fluoro-5'-uridylate
Di-p-chlorophenyl 2'-deoxy-5-fluoro-5'-uridylate Di-p-chlorophenyl 3-formyl-2'-deoxy-5-fluoro-5'-uridylate
Di-p-chlorophenyl 3'-O-acetyl-2'-deoxy-5-fluoro-5'-uridylate
Di-p-chlorophenyl 3'-O-butyryl-2'-deoxy-5-fluoro-5'-uridylate
Di-p-chlorophenyl 3'-O-benzoyl-2'-deoxy-5-fluoro-5'-uridylate
Di-p-chlorophenyl 3'-O-m-methylbenzoyl-2'-deoxy-5-fluoro-5'-uridylate
Di-p-chlorophenyl 3-acetyl-2'-deoxy-5-fluoro-5'-uridylate
Di-p-chlorophenyl 3-benzoyl-2'-deoxy-5-fluoro-5'-uridylate
Di-p-chlorophenyl 3-m-methylbenzoyl-2'-deoxy-5-fluoro-5'-uridylate
Di-p-chlorophenyl 3-(3,4-methylenedioxybenzoyl)-2'-deoxy-5-fluoro-5'-uridylate
Di-p-chlorophenyl 3'-O-acetyl-3-benzoyl-2'-deoxy-5-fluoro-5'-uridylate
Di-m-bromophenyl 2'-deoxy-5-fluoro-5'-uridylate
Di-p-bromophenyl 3'-O-hexanoyl-2'-deoxy-5-fluoro-5'-uridylate
Di-p-bromophenyl 2'-deoxy-5-fluoro-5'-uridylate
Di-m-trifluoromethylphenyl 2'-deoxy-5-fluoro-5'-uridylate
Di-m-trifluoromethylphenyl 3'-O-propionyl-2'-deoxy-5-fluoro-5'-uridylate
Di-m-trifluoromethylphenyl 3'-O-butyryl-2'-deoxy-5-fluoro-5'-uridylate
Di-p-trifluoromethylphenyl 2'-deoxy-5-fluoro-5'-uridylate
Di-p-trifluoromethylphenyl 3-(3,4-methylenedioxybenzoyl)-2'-deoxy-5-fluoro-5'-uridylate
Di-o-cyanophenyl 2'-deoxy-5-fluoro-5'-uridylate
Di-m-cyanophenyl 2'-deoxy-5-fluoro-5'-uridylate
Di-p-cyanophenyl 2'-deoxy-5-fluoro-5'-uridylate
Di-p-cyanophenyl 3-m-methoxybenzoyl-2'-deoxy-5-fluoro-5'-uridylate
Di-o-nitrophenyl 2'-deoxy-5-fluoro-5'-uridylate
Di-o-nitrophenyl 3-hexanoyl-2'-deoxy-5-fluoro-5-uridylate
Di-m-nitrophenyl 2'-deoxy-5-fluoro-5'-uridylate
Di-p-nitrophenyl 2'-deoxy-5-fluoro-5'-uridylate
Di-p-nitrophenyl 3'-O-acetyl-2'-deoxy-5-fluoro-5'-uridylate
Di-p-nitrophenyl 3-(3,4-methylenedioxybenzoyl) 2'-deoxy-5-fluoro-5'-uridylate
Di-p-carboxyphenyl 2'-deoxy-5-fluoro-5'-uridylate
Di-p-carboxyphenyl 3-(1-naphthoyl)-2'-deoxy-5-fluoro-5'-Di(3,4-methylenedioxyphenyl) 2'-deoxy-5-fluoro-5'-uridylate
Di(3,4-methylenedioxyphenyl) 3'-butyryl-2'-deoxy-5-fluoro-5'-uridylate
Di(2,3-dichlorophenyl) 2'-deoxy-5-fluoro-5'-uridylate
Di(2,4-dichlorophenyl) 2'-deoxy-5-fluoro-5'-uridylate
Di(2,4-dichlorophenyl) 3'-O-acetyl-2'-deoxy-5-fluoro-5'-uridylate
Di(3,4-dichlorophenyl) 2'-deoxy-5-fluoro-5'-uridylate
Di(3,5-dichlorophenyl) 2'-deoxy-5-fluoro-5'-uridylate
Di(4-chloro-3-methylphenyl) 2'-deoxy-5-fluoro-5'-uridylate
Di(2-bromo-4-methylphenyl) 2'-deoxy-5-fluoro-5'-uridylate
Di(2-chloro-4-nitrophenyl) 2'-deoxy-5-fluoro-5'-uridylate
Di(3,4-dimethylphenyl) 3'-O-acetyl-2'-deoxy-5-fluoro-5'-uridylate
Di(2,3,5-trichlorophenyl) 2'-deoxy-5-fluoro-5'-uridylate
Di(2,3,5-trimethylphenyl) 2'-deoxy-5-fluoro-5'-uridylate
Di-1-naphthyl 2'-deoxy-5-fluoro-5'-uridylate
Di-2-naphthyl 2'-deoxy-5-fluoro-5'-uridylate
Di-4-methoxycarbonylphenyl 2'-deoxy-5-fluoro-5'-uridylate
Di(2,4-dichloro-1-naphthyl) 2'-deoxy-5-fluoro-5'-uridylate
Dibenzyl 2'-deoxy-5-fluoro-5'-uridylate
Di(4-chloro-3-nitrobenzyl) 2'-deoxy-5-fluoro-5'-uridylate
2'-Deoxy-5-fluorouridine 5'-(S,S-diphenylphosphorodithioate)
2'-Deoxy-5-fluorouridine 5'-(S,S-di-p-methoxyphenylphosphorodithioate)
2'-Deoxy-5-fluorouridine 5'-(S,S-di-p-chlorophenylphosphorodithioate)
p-Chlorophenyl phenyl 2'-deoxy-5-fluoro-5'-uridylate
p-Chlorophenyl phenyl 2'-deoxy-5-fluoro-3'-uridylate
p-Chlorophenyl p-bromophenyl 2'-deoxy-5-fluoro-5'-uridylate
4-Chloro-3-methylphenyl phenyl 2'-deoxy-5-fluoro-5'-uridylate
Methyl phenyl 2'-deoxy-5-fluoro-5'-uridylate
n-Butyryl phenyl 2'-deoxy-5-fluoro-5'-uridylate
n-Dodecyl phenyl 2'-deoxy-5-fluoro-5'-uridylate
Citroneryl phenyl 2'-deoxy-5-fluoro-5'-uridylate
Geranyl phenyl 2'-deoxy-5-fluoro-5'-uridylate
Citroneryl p-chlorophenyl 2'-deoxy-5-fluoro-5'-uridylate Among the 2'-deoxy-5-fluorouridine derivatives of the formula (I), the following are preferable compounds. That is, the compounds of the formula (I) wherein $R^2$ is a group of the formula (V) and both $R^1$ and $R^3$ are hydrogen atom; the compounds of the formula (I) wherein $R^2$ is a group of the formula (V), $R^1$ is hydrogen atom and $R^3$ is an acyl group; the compounds of the formula (I) wherein $R^2$ is a group of the formula (V), $R^1$ is an acyl group and $R^3$ is hydrogen atom; and the compounds of the formula (I) wherein $R^2$ is a group of the formula (V) and group of the formula (V). As $R^1$ and $R^3$, preferred is hydrogen atom or an acyl group respectively. Particularly preferred are the compounds of the formula (I) wherein $R^2$ is a group of the formula (v) and both of $R^1$ and $R^3$ are hydrogen atom. As the group of the formula (V), preferred are the groups of the formula (V) wherein each of $R^4$ and $R^5$ is phenyl group or a phenyl group having substituent(s) and $X^1$ and $X^2$ are both oxygen atom or sulfur atom. As the substituents, preferred are chlorine atom, fluorine atom, bromine atom, trifluoromethyl group, nitro group, cyano group, methoxycarbonyl group, acetyl group and methyl group. The phenyl group having substituent(s) may have one substituent or at least two substituents selected from the above-mentioned substituents. When the phenyl group has at least two substituents, the two or more substituents may be the same or different. As the group of the formula (V), particularly preferred are the groups of the formula (V) wherein both of $X^1$ and $X^2$ represent oxygen atom and both of $R^4$ and $R^5$ respectively represent a phenyl group having as the substituent(s) one or two chlorine atom, fluorine atom, bromine atom and/or trifluoromethyl group.

The 2'-deoxy-5-fluorouridine derivatives of the formula (I) can be synthesized in accordance with the A method or B method as shown below.

(A method)

A method which comprises reacting a compound of the formula

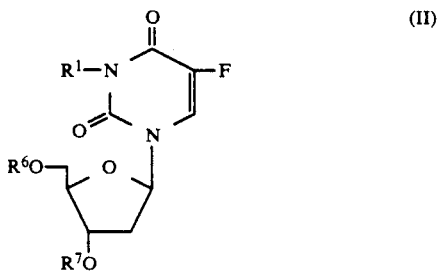

wherein $R^1$, $R^6$ and $R^7$ are respectively as defined above with a compound of the formula

wherein $X^1$, $X^2$, $R^4$ and $R^5$ are respectively as defined above and Y is a halogen atom and, if necessary, deprotecting the reaction product for the hydroxyl group-protecting group.

In the compounds of the formula (II), as the hydroxyl group-protecting group represented by $R^6$ and $R^7$, there may be mentioned acyl groups such as formyl, acetyl, butyryl, benzoyl, m-methylbenzoyl and p-chlorobenzoyl; methyl group; substituted alkyl groups such as tetrahydropyranyl and 2-methoxyethoxymethyl group; silyl groups such as trimethylsilyl and dimethyl-t-butylsilyl and triaryl-substituted methyl groups such as trityl, 4-methoxytrityl and 4,4'-dimethoxytrityl. These compounds of the formula (II) can be synthesized in accordance with the conventional manner. For example, 5'-O-trityl-2'-deoxy-5-fluorouridine and 3'-O-acetyl-2'-deoxy-5-fluorouridine can be synthesized by a method by J. A. Montgomery [See the Journal of Medical and Pharmaceutical Chemistry 5, 24 (1962)].

The compounds of the formula (III) can be in general synthesized by a conventional dehalogenation reaction of an alcohol or a thiol with a phosphorus oxyhalide or its derivative representable by the following reaction formula

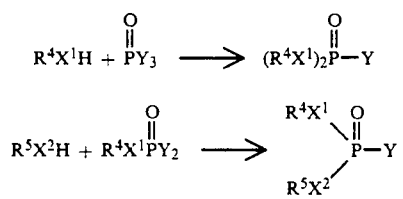

wherein $X^1$, $X^2$, $R^4$, $R^5$ and Y are respectively as defined above. As the halogen atom represented by Y, chlorine atom and bromine atom are preferable. As the reaction solvent, preferred are aprotic organic solvents which dissolve the base highly but do not prevent the reaction from proceeding. As such preferred solvents, there are mentioned pyridine, chloroform, dichloromethane, dioxane, tetrahydrofuran, benzene, toluene, dimethylsulfoxide, acetonitrile and the like. The reaction temperature ranges generally from −10° C. to 100° C. The reaction time ranges generally from about 1 hour to 24 hours. The reaction is preferably conducted in the presence of a base. As such bases, there may be mentioned organic bases exemplified by tertiary amines such as pyridine, triethylamine and N,N-dimethylaniline and inorganic bases such as sodium hydrogen carbonate, potassium carbonate and sodium acetate.

The reaction of the compound of the formula (II) with the compound of the formula (III) can be conducted under the conditions of conventional dehalogenation reactions. The compoud of the formula (III) is used at least in an equimolar amount, preferably in about 1 to 3 times molar amount, relative to the amount of the compound of the formula (II) to be used. As the reaction solvent to be used, preferred are aprotic organic solvents which dissolve the base highly but do not prevent the reaction from proceeding. As the preferred solvents, mention is made of tertiary amines such as pyridine, triethylamine and picoline; halogenated hydrocarbons such as chloroform and dichloromethane; ethers such as dioxane and tetrahydrofuran; aromatic hydrocarbons such as benzene and toluene; N,N-dimethylacetamide; dimethylsulfoxide; acetonitrile and the like. The reaction temperature generally ranges from −30° C. to 100° C., preferably from −10° C. to room temperature. The reaction time generally ranges from about 1 hour to 3 days, preferably from 1 hour to 24 hours. The reaction is conducted preferably in the presence of a base. As the base to be used, there are mentioned organic bases such as tertiary amines exemplified by pyridine, triethylamine and N,N-dimethylaniline, or inorganic bases such as sodium hydrogen carbonate, potassium carbonate and sodium acetate.

(B method)

A method which comprises reacting a compound of the formula (II) with a compound of the formula

wherein $X^1$, $X^2$, $R^4$, $R^5$ and $R^8$ are respectively as defined above in the presence of a condensating agent, and, if necessary, deprotecting the reaction product for the hydroxyl group-protecting group.

The compound of the formula (IV) can be obtained, for example, by hydrolysis of the compound of the formula (III). The compound of the formula (IV) wherein $X^1$ and $X^2$ are both sulfur atom can be obtained, for example, by condensating methylphosphorodichloridate with a thiol, followed by hydrolysis of the obtained condensate [See the Chemistry Letters 507 (1978)].

The reaction of the compound of the formula (II) with the compound of the formula (IV) can be conducted under the conditions of conventional condensation reactions. The compound of the formula (IV) is used at least in an equimolar amount, preferably in about 1 to 3 times molar amount, relative to the amount of the compound of the formula (II). As the condensating agent, there are preferably used carbodiimides such as dicyclohexylcarbodiimide and 1-ethyl-3-(3-dimethylaminopropyl)carbodiimide, arylsulfonylchlorides such as 2,4,6-triisopropylbenzenesulfonylchloride, benzenesulfonylchloride, p-toluenesulfonylchloride, 2,4,6-trimethylbenzenesulfonylchloride and 8-quinolinesulfonylchloride, arylsulfonamides such as 2,4,6-trimethylbenzenesulfonylimidazolide, 2,4,6-triisopropylbenzenesulfonylimidazolide, 2,4,6-trimethylbenzenesulfonyltriazolide, 2,4,6-triisopropylbenzenesulfonyltriazolide, 2,4,6-trimethylbenzenesulfonyl-3-nitrotriazolide, 2,4,6-triisopropylbenzenesulfonyl-3-nitrotriazolide; azo compounds and phosphines such as diethylazodicarboxylate and triphenylphosphine, and diisopropylazodicarboxylate and triphenylphosphine [See Bulletin of the Chemical Society of Japan 52 (4) 1191 (1979)]. As the reaction solvent, preferred are aprotic organic solvents in which the base is highly soluble and which do not prevent the reaction from preceeding. As the preferred solvents, there may be mentioned pyridine, N,N-dimethylformamide, N,N-dimethylacetamide, dimethylsulfoxide, hexamethylphosphoramide, ethyl acetate, tetrahydrofuran, dimethoxyethane, dioxane, chloroform and methylene chloride, which are singly or in mixture used respectively. In the condensation reactions, as the condensation-auxiliary, use is sometimes made of, for example, organic bases such as triethylamine, tributylamine, pyridine, picoline, γ-dimethylaminopyridine and dimethylaniline. The reaction time is generally within the range from about one hour to 3 days. The reaction temperature generally ranges from −30° C. to 100° C., preferably 0° C. to room temperature.

The compounds of the formula (II) wherein $R^1$ is an acyl group can be synthesized in a conventional manner, for example, by acid chloride method [See, the gazette of Tokkai No. 61591/1985, the Chemistry Letters 1051 (1983)].

The 2'-deoxy-5-fluorouridine derivatives of the formula (I) wherein $R^1$ is an acyl group can also be obtained by reacting the compounds of the formula (II) wherein $R^1$ is hydrogen atom with the compounds of the formula (III) or that of the formula (IV) to obtain the compounds of the formula (I) wherein $R^1$ is hydrogen atom, followed by the reaction of the obtained product with the corresponding acid chloride in accordance with a conventional method.

The 2'-deoxy-5-fluorouridine derivatives of the formula (I) obtained by the above-mentioned A method or B method can be isolated and purified by selecting a suitable procedure among re-precipitation, extraction, silica gel chromatography, high performance liquid chromatography, recrystallization and other conventional operations to apply or conduct, in some cases, in combination.

In the following, shown are the results of the tests for antitumour effects and acute toxicity of 2'-deoxy-5-fluorouridine derivatives of the formula (I).

TEST EXAMPLE 1

Measurement of antitumour activity value

Mouse transplantable tumour Sarcoma 180 cells ($5 \times 10^6$ cells) were transplanted subcutaneously into male ICR/JCL mice (weighing 27–30 g) in the back. The test compounds were dissolved or suspended in a 0.5 weight % aqueous solution of CMC containing Tween 80 at the concentration of 0.1 weight % to afford test preparations. Using 7 animals per group, the test preparations were orally administered to each mouse at the dose of 0.1 ml/10 g mouse body weight once a day for consecutive 9 days from the following day of the day when the tumours were transplanted. To the control group, the above-mentioned test preparations, which does not contain any test compouds, were administered in the same manner.

On the twelfth day from the day of tumour-transplantation, the average weight of tumours for each of the test compounds at the respective doses was measured. The weight was compared with the average weight of the tumours of the control group, and the tumour proliferation-inhibitory rates of the test compounds based on that of the control group were estimated at the respective dose.

From the test values, estimated were the doses at which tumour proliferation-inhibitory rate is over 50% ($ED_{50}$), and the doses were deemed as the antitumour activity value of the respective test compounds.

TABLE 1

| | Test Compound [formula (I)] | | | $ED_{50}$ |
|---|---|---|---|---|
| | $R^1$ | $R^2$ | $R^3$ | (mg/kg) |
| Compound obtained in Ex. 1 | H | −P(O−⌬)₂ with =O | H | 11.1 |
| Compound obtained in Ex. 3 | −C(=O)−⌬ | −P(O−⌬)₂ with =O | H | 7.0 |
| Compound obtained in Ex. 5 | H | −P(=O)(O−⌬)(O−CH₂CH₂CH(CH₃)CH₂CH₂CH=C(CH₃)₂) | H | 23.8 |

TABLE 1-continued

| | Test Compound [formula (I)] | | | $ED_{50}$ |
|---|---|---|---|---|
| | $R^1$ | $R^2$ | $R^3$ | (mg/kg) |
| Compound obtained in Ex. 6 | H | $-\overset{\overset{O}{\|}}{P}(\text{O-C}_6\text{H}_5)(\text{O-C}_6\text{H}_3(\text{CH}_3)(\text{Cl}))$ | H | 6.2 |
| Compound obtained in Ex. 7 | H | $-\overset{\overset{O}{\|}}{P}(\text{O-C}_6\text{H}_4\text{-Cl})_2$ | H | 1.4 |
| Compound obtained in Ex. 8 | H | $-\overset{\overset{O}{\|}}{P}(\text{O-C}_6\text{H}_4\text{-Cl})_2$ (2-Cl) | H | 10.0 |
| Compound obtained in Ex. 9 | H | $-\overset{\overset{O}{\|}}{P}(\text{O-C}_6\text{H}_4\text{-Cl})_2$ (3-Cl) | H | 1.4 |
| Compound obtained in Ex. 10 | H | $-\overset{\overset{O}{\|}}{P}(\text{O-C}_6\text{H}_3\text{Cl}_2)_2$ (2,3-Cl$_2$) | H | 3.6 |
| Compound obtained in Ex. 11 | H | $-\overset{\overset{O}{\|}}{P}(\text{O-C}_6\text{H}_3\text{Cl}_2)_2$ (2-Cl, 4-Cl) | H | 1.5 |
| Compound obtained in Ex. 12 | H | $-\overset{\overset{O}{\|}}{P}(\text{O-C}_6\text{H}_3\text{Cl}_2)_2$ (3-Cl, 4-Cl) | H | 2.5 |
| Compound obtained in Ex. 13 | H | $-\overset{\overset{O}{\|}}{P}(\text{O-C}_6\text{H}_3(\text{OCH}_2\text{CH}_2\text{O}))_2$ | H | 25.0 |
| Compound obtained in Ex. 16 | H | $-\overset{\overset{O}{\|}}{P}(\text{O-C}_6\text{H}_4\text{-CN})_2$ | H | 6.1 |
| Compound obtained in Ex. 17 | H | $-\overset{\overset{O}{\|}}{P}(\text{O-C}_6\text{H}_4\text{-F})_2$ | H | 1.3 |
| Compound obtained in Ex. 18 | H | $-\overset{\overset{O}{\|}}{P}(\text{O-C}_6\text{H}_4\text{-Br})_2$ | H | 1.2 |

TABLE 1-continued

| | Test Compound [formula (I)] | | | $ED_{50}$ |
|---|---|---|---|---|
| | $R^1$ | $R^2$ | $R^3$ | (mg/kg) |
| Compound obtained in Ex. 19 | H | $-\text{P(O}-\!\!\bigcirc\!\!-\text{CF}_3)_2$ with P=O | H | 0.9 |
| Compound obtained in Ex. 22 | H | $-\text{P(O}-\!\!\bigcirc\!\!-\text{Cl})_2$ with P=O | $-\overset{O}{\overset{\|}{C}}CH_3$ | 1.2 |
| Compound obtained in Ex. 24 | H | $-\text{P(O}-\!\!\bigcirc\!\!-\text{NO}_2)_2$ with P=O | H | 5.4 |
| Compound obtained in Ex. 25 | H | $-\text{P(S}-\!\!\bigcirc\!\!-)_2$ with P=O | H | 9.8 |
| Compound obtained in Ex. 26 | H | $-\text{P(S}-\!\!\bigcirc\!\!-\text{Cl})_2$ with P=O | H | 4.2 |
| FdUrd | H | H | H | 59.5 |

TEST EXAMPLE 2

Measurement of acute toxicity value

Male ICR/JCL mice (weighing 27-30 g), 5 animals per group, were used for the test. The test compounds were dissolved or suspended in a 0.5 weight % aqueous solution of CMC containing Tween 80 at the concentration of 0.1 weight % to give test preparations.

The test preparations were orally administered at the dose of 0.1 ml/10 g mouse body weight. Over the period of 3 weeks from the beginning of the test, the general toxic symptom, change in body weight and incidence of death were observed every day. Estimation of acute toxicity value ($LD_{50}$) was conducted after 3 weeks' lapse from respective administration by the up-and-down method.

The $LD_{50}$ values (mg/kg) of all the test compounds shown in Table 1 were not less than 2000 mg/kg which is the administrable maximum dose.

As apparent from Table 1, the 2'-deoxy-5-fluorouridine derivatives of the formula (I) exhibit excellent antitumour activities as compared with FdUrd (Control compound). Among others, the 2'-deoxy-5-fluorouridine derivatives of the formula (I) wherein $R^2$ is a group of the formula (V), and $R^4$ and $R^5$ are respectively a phenyl group which may be substituted by chlorine atom, fluorine atom, bromine atom, trifluoromethyl group, cyano group, nitro group, methyl group and/or so on possess excellent activities. In particular, the 2'-deoxy-5-fluorouridine derivatives of the formula (I) wherein $R^4$ and $R^5$ are respectively a phenyl group which may be substituted by one or two selected from chlorine atom, fluorine atom, bromine atom and/or trifluoromethyl group and, $X^1$ and $X^2$ are both oxygen atom exhibit extremely potent antitumour activities, 40 to 70 times as high tumour proliferation-inhibitory effect as FdUrd (control compound) in terms of $ED_{50}$.

The 2'-deoxy-5-fluorouridine derivatives of the formula (I) have very low toxicity, as is evident from the results of the measurement of acute toxicity value. The 2'-deoxy-5-fluorouridine derivatives of the formula (I) have reduced toxicities and side effects such as digestive tract disorder, cytopenia (decrease in the number of leukocyte) and reduction in body weight, and show high therapeutic index.

Said 2'-deoxy-5-fluorouridine derivatives exhibit superior effects in the treatment of cancers whether they are administered orally or with injection.

When the 2'-deoxy-5-fluorouridine derivatives of the formula (I) of the present invention are used as an antitumour agent, namely, antitumour composition, they are usually prepared to be in dosage forms suitable for the administration route in combination with pharmacologically acceptable suitable carriers They may be, for example, in forms for oral administration such as tablets, pills, capsules, granules, powders, liquids and so on or in forms for non-oral administration such as intravenous or intramuscular injections, suppositories and the like.

These dosage forms can be produced by the methods for the production of pharmaceutical preparations known to and conventionally used by those skilled in the art. In producing solid pharmaceutical preparations for oral administration, to the effective ingredients of the present invention (the 2'-deoxy-5-fluorouridine derivatives of the formula (I)) are added excipients, if necessary, binders, disintegrants, lubricants, coloring agents, corrigent agents, flavoring agents, and the like, and then the mixture can be formulated into tablets, coated tablets, granules, powders, capsules and the like by a conventional method. In producing injectable preparations, the effective ingredients of the present invention are diluted with diluents, whereto pH adjusting agents, buffers, stabilizers, isotonicizing agents, topical anesthetics and the like are added, and subcutaneous, intramuscular and intravenous injections can be produced by a conventional method. In producing suppositories, bases and, if necessary, surfactants and the like are added to the effective ingredients of the present invention, and thereafter suppositories can be produced by a conventional method.

In producing tablets, capsules, granules and powders, as the excipients, use is made of, for example, lactose, sucrose, starch, talc, magnesium stearate, calcium stearate, crystalline cellulose, methyl cellulose, carboxymethyl cellulose, glycerine, sodium arginate, arabic gum and the like; as the binders, use is made of polyvinylalcohol, polyvinylether, ethyl cellulose, arabic gum, shellac, white sugar and the like; as the lubricants, use is made of magnesium stearate, talc and the like, and as other coloring agents, disintegrators and the like, use is made of conventional and known ones. Tablets may be coated by a conventional method.

As the diluents for producing injections, there can be used water, ethylalcohol, macrogol, propylene glycol, ethoxyisostearyl alcohol, isostearyl alcohol polyoxide, polyoxy ethylenesorbitan fatty acid esters and the like. In this case, sodium chloride, glucose or glycerine may be incorporated in the pharmaceutical preparations in an amount enough to adjust the solution to an isotonicized one. Besides, conventional pH adjusting agents, buffers, stabilizers, topical anesthetics and the like may be added thereto.

As the bases for producing suppositories, use can be made of, for example, greasy bases such as cacao butter, polyethylene glycol, lanolin, fatty acid triglycerides and Witepsol (Registered trade mark by Dynamite Novel Corp.) and the like or water-soluble bases such as macrogols.

While the amount of the effective ingredients of the present invention to be incorporated in the respective unit dosage forms as mentioned above varies depending upon the forms of the pharmaceutical compositions, the solubility and chemical properties of the compounds, administration route, administration project and the like, it may be generally, per the unit of the dosage form, approximately 10-200 mg for oral administration, approximately 100-1000 mg for injections and approximately 100-2000 mg for suppositories.

While the daily dose of the medicinal composition in the above-mentioned dosage form should be determined adequately in accordance with the symptom, the age and sex of the administration host and and the like, the daily dose in the case of oral administration is about 50-200 mg per adult, which is to be administered in 2 to 4 times divided doses a day. In the case of injections, for example, the daily dose for intravenous injections is 10-1000 mg, which is to be, if necessary, diluted with physiological saline or glucose injectable solution in conjunction with ethyl alcohol, macrogol, propylene glycol, polyoxyethylenesorbitan fatty acid ester and the like to be administered once a day. In the case of suppositories, the daily dose is generally 50-1000 mg per adult, which is to be rectally administered in once to four times divided doses at intervals of 6 to 24 hours. The antitumour compositions containing as the effective ingredients the 2'-deoxy-5-fluorouridine derivatives as mentioned above permit the derivatives to exhibit their own excellent antitumour actions effectively.

Hereafter, examples for the production of 2'-deoxy-5-fluorouridine derivatives of the formula (I) are shown as the working examples The present invention should not be limited to the working examples Shown are the results of analyses by Nuclear Resonance Spectra of the compounds obtained in the respective working examples, which were all measured with the use of TMS as the internal standard.

EXAMPLE 1

Production of diphenyl 2'-deoxy-5-fluoro-5'-uridylate

Diphenylphosphorochloridate [1.1 g (4.11 mmol)] was cooled to $-10°$ C. to $0°$ C. in an ice-water bath. Thereto, 1.0 g (4.06 mmol) of 2'-deoxy-5-fluorouridine dissolved in 15 ml of pyridine was added dropwise over the period of 20 minutes. After the completion of the dropwise addition, the mixture was stirred at room temperature overnight. To the reaction mixture was added 50 ml of toluene, and the solvent was distilled off under reduced pressure. Thereafter, 50 ml of toluene was again added to the residue, and the solvent was distilled off under reduced pressure. The obtained residue was subjected to silica gel column chromatography with chloroform-methanol (9:1 v/v) as the eluent to give 910 mg of diphenyl 2'-deoxy-5-fluoro-5'-uridylate in a glassy form (Yield 41%).

$^1$H—NMR (CDCl$_3$) δ (ppm) 9.93 (1H, broad s, N$_3$—H) 7.52 (1H, d, J=6 Hz, C$_6$—H) 7.38-7.03 (10H, m, Ar—H) 6.27-6.10 (1H, m, C$_{1'}$—H) 4.51-4.33 (3H, m, C$_3'$,5'—H) 4.13-4.00 (1H, m, C$_{4'}$—H) 2.46-1.70 (3H, m, C$_{2'}$—H, OH).

EXAMPLE 2

Production of diphenyl 2'-deoxy-5'-O-(diphenoxyphosphinyl)-5-fluoro-3'-uridylate [The compound of the formula (I) wherein $R^1$=H; $R^2,R^3$=(PhO)$_2$P(=O)— (Ph stands for phenyl group.)]

Diphenylphosphorochloridate [160 mg (0.63 mmol)] was cooled to $-10°$ to $0°$ C. in an ice-water bath, whereto 100 mg (0.41 mmol) of 2'-deoxy-5-fluorouridine dissolved in 2 ml of pyridine was added dropwise over the period of 5 minutes. After the completion of the dropwise addition, the mixture was stirred at room temperature overnight. After the solvent was distilled off under reduced pressure, water was added to the residue, followed by extraction with chloroform The extract was washed with water and dried over anhydrous magnesium sulfate After the solvent was distilled off from the extract under reduced pressure, the obtained residue was purified by silica gel thin layer column chromatograph (PLC plate manufactured by Merck AG. Silica gel 60F$_{254}$s with concentrated zone; developing solvent: ethyl acetate) to 120 mg of diphenyl 2'-deoxy-5'-O-(diphenoxy phosphinyl)-5-fluoro-3'-uridylate in an oily form (Yield 42%).

$^1$H—NMR (CDCl$_3$) δ (ppm) 9.87 (1H, broad s, N$_3$—H) 7.58 (1H, d, J=6 Hz, C$_6$—H) 7.50-7.17 (20H, m, Ar—H) 6.40-6.23 (1H, m, C$_{1'}$—H) 5.37-5.21 (1H, m, C$_{3'}$—H) 4.57-4.28 (3H, m, C$_{4'}$,5'—H) 2.67-1.82 (2H, m, C$_{2'}$—H).

EXAMPLE 3

Production of diphenyl 3-benzoyl-2'-deoxy-5-fluoro-5'-uridylate

Diphenylphosphorochloridate [1.05 g (3.9 mmol)] was cooled to $-10°$ C. to $0°$ C. in an ice-water bath, whereto, 1.24 g (3.54 mmol) of 3-benzoyl-2'-deoxy-5-fluorouridine dissolved in 10 ml of pyridine was added dropwise over the period of 20 minutes. After the completion of the dropwise addition, the mixture was stirred at room temperature overnight. To the reaction mixture was added 50 ml of toluene, and the solvent was distilled off under reduced pressure. To the obtained residue was again added 50 ml of toluene. Thereafter, the solvent was distilled off under reduced pressure. The obtained residue was subjected to silica gel column chromatography with the use of a mixture of ethyl acetate and benzene (3:2 v/v) as the eluent to give 810 mg of diphenyl 3-benzoyl- 2'-deoxy-5-fluoro-5'-uridylate in a glassy form (Yield 33%).

$^1$H—NMR (CDCl$_3$) δ (ppm) 7.87–7.01 (16H, m, C$_6$—H, Ar—H) 6.17–6.03 (1H, m, C$_1$'—H) 4.40–4.23 (3H, m, C$_3$',5'—H) 4.05–3.88 (1H, m, C$_4$'—H) 3.47 (1H, broad s, OH) 2.33–1.66 (2H, m, C$_2$'—H)

EXAMPLE 4

Production of diphenyl 2'-deoxy-5-fluoro-3'-uridylate

Diphenylphosphorochloridate [0.9 g (3.35 mmol)] was cooled to −10° C. to 0° C. in an ice-water bath, whereto 1.3 g (2.66 mmol) of 5'-trityl-2'-deoxy-5-fluorouridine dissolved in 10 ml of pyridine was added dropwise over the period of 20 minutes. After the completion of the dropwise addition, the mixture was stirred at room temperature overnight. To the reaction mixture was added 50 ml of toluene, and the solvent was distilled off under reduced pressure. After 50 ml of toluene was again added to the obtained residue, the solvent was distilled off under reduced pressure. The obtained residue was dissolved in 100 ml of chloroform. The solution was washed with water, a dilute aqueous solution of sodium hydroxide and water in order, and was dried over anhydrous magnesium sulfate. Thereafter, the solvent was distilled off under reduced pressure to afford 2.0 g of crude product of diphenyl 5'-trityl-2'-deoxy-5-fluoro-3'-uridylate. To this crude product was added 15 ml of a 80% aqueous solution of acetic acid, and the mixture was heated at 80° C. for 7 hours. The solvent was distilled off from the reaction mixture under reduced pressure, followed by addition of water. The solvent was again distilled off under reduced pressure. To the obtained residue was added 100 ml of chloroform, and the mixture was washed with water three times and dried over anhydrous magnesium sulfate. After the solvent was distilled off under reduced pressure, the obtained residue was subjected to silica gel column chromatography with the use of a mixture of ethyl acetate and benzene (3:2 v/v) as the eluent to give 900 mg of diphenyl 2'-deoxy-5-fluoro-3'-uridylate in a glassy form (Yield 71%).

$^1$H—NMR (CDCl$_3$) δ (ppm) 9.34 (1H, broad s, N$_3$—H) 7.91 (1H, d, J=6 Hz, C$_6$—H) 7.47–7.10 (10H, m, Ar—H) 6.32–6.17 (1H, m, C$_1$'—H) 5.37–5.17 (1H, m, C$_3$'—H) 4.23–4.10 (1H, m, C$_4$'—H) 3.85–3.72 (2H, m, C$_5$'—H) 2.63–1.92 (3H, m, C$_2$'—H, OH)

EXAMPLE 5

Production of citroneryl phenyl 2'-deoxy-5-fluoro-5'-uridylate

Phenylphosphorodichloridate [1.92 ml (12.58 mmol)] was dissolved in 20 ml of tetrahydrofuran, and the solution was cooled to −10° C. to 0° C. in an ice-water bath. To this solution was added dropwise a mixture of 2.0 g (12.80 mmol) of citronerol, 1.8 ml (12.91 mmol) of triethylamine and 10 ml of tetrahydrofuran over the period of 1 hour. After the completion of the dropwise addition, the mixture was stirred at room temperature overnight. The resulting precipitation was filtered and washed with petroleum ether (30° C. to 60° C.). From the obtained filtrate, the solvent was distilled off under reduced pressure The obtained residue was subjected to silica gel column chromatography with the use of chloroform as the eluent to give 2.3 g of citroneryl phenylphosphorochloridate in an oily form (Yield 54%).

The obtained citroneryl phenylphosphorochloridate [1.30 g (3.93 mmol)] was cooled to −10° C. to 0° C. in an ice-water bath.

Thereto, 850 mg (3.45 mmol) of 2'-deoxy-5-fluorouridine as dissolved in 17 ml of pyridine was added dropwise over the period of 20 minutes. After the completion of the dropwise addition, the mixture was stirred at room temperature overnight. To the reaction mixture was added 50 ml of toluene. After the solvent was distilled off under reduced pressure, 50 ml of toluene was again added to the residue. The solvent was distilled off under reduced pressure The obtained residue was subjected to silica gel column chromatography with the use of a mixture of chloroform and methanol (9:1 v/v) as the eluent to give 1.27 g of citroneryl phenyl 2'-deoxy-5-fluoro-5'-uridylate in a glassy form (Yield 68%).

$^1$H—NMR (CDCl$_3$) δ (ppm) 9.60 (1H, broad s, N$_3$—H) 7.65, 7.58 (1H, d, d, J=6.6 Hz, C$_6$—H) 7.40–7.10 (5H, m, Ar—H) 6.32–6.17 (1H, m, C$_1$'—H) 5.08–4.92 (1H, m, C$_6$''—H) 4.50–4.07 (7H, m, C$_3$',4',5'—H, C$_1$''—H, OH) 2.57–1.70 (4H, m, C$_2$'—H, C$_5$''—H) 1.62, 1.53 (6H, s, s, C$_7$'''—CH$_3$) 1.47–1.07 (5H, m, C$_2$'',3'',4''—H) 0.82 (3H, d, J=4.5 Hz, C$_''$—CH$_3$).

EXAMPLE 6

Production of 4-chloro-3-methylphenyl phenyl 2'-deoxy-5-fluoro-5'-uridylate

By the same method as in Example 5, 4-chloro-3-methylphenyl phenyl 2'-deoxy-5-fluoro-5'-uridylate was obtained in a glassy form (Yield 61%).

$^1$H—NMR (CDCl$_3$) δ (ppm) 7.62, 7.60 (1H, d, d, J=6, 6 Hz, C$_6$—H) 7.57–6.93 (8H, m, Ar—H) 6.37–6.17 (1H, m, C$_1$'—H) 4.60–4.40 (3H, m, C$_3$',5'—H) 4.21–4.06 (1H, m, C$_4$'—H) 2.34 (3H, s, CH$_3$) 2.53–1.80 (2H, m, C$_2$'—H).

EXAMPLE 7

Production of di-p-chlorophenyl 2'-deoxy-5-fluoro-5'-uridylate

In 100 ml of benzene was dissolved 3.07 g (20 mmol) of phosphorus oxychloride, and the solution was cooled in an ice-water bath. To this cooled solution was added dropwise a mixture of 5.14 g (40 mmol) of p-chlorophenol, 4.05 g (40 mmol) of triethylamine and 20 ml of benzene over the period of 15 minutes. After the completion of the dropwise addition, the mixture was heated under reflux for 3 hours. The suction filtration of the reaction mixture was conducted with a short column which was comprised of a glass filter of 7 cm in diameter filled with silica gel layer, anhydrous magnesium sulfate layer and sea sands layer of about 1 cm in thickness respectively in order thereon. The eluate was washed with benzene to adjust the volume of the resulting eluate amount to 200 ml. The solvent was distilled off under reduced pressure to give 5.84 g of di-p-chlorophenylphosphorochloridate in an oily form (Yield 86%).

Di-p-chlorophenylphosphorochloridate [1.25 g (3.70 mmol)] obtained in the above-mentioned manner was cooled to −10° C. to 0° C. in an ice-water bath. Thereto, 700 mg (2.84 mmol) of 2'-deoxy-5-fluorouridine as dissolved in 10 ml of pyridine was added dropwise over the period of 20 minutes. After the completion of the dropwise addition, the mixture was stirred at room temperature overnight. To the reaction mixture was added 50 ml of toluene, and the solvent was distilled off under reduced pressure. Thereafter, 50 ml of toluene was again added to the obtained residue, and the solvent was distilled off under reduced pressure. The obtained residue was subjected to silica gel column chromatography with the use of a mixture of chloroform and methanol (9:1 v/v) as the eluent to give 1.00 g of di-p-chlorophenyl 2'-deoxy-5-fluoro-5'-uridylate in a glassy form (Yield 64%).

$^1$H—NMR (CDCl$_3$) δ (ppm) 9.97 (1H, broad s, N$_3$—H) 7.62 (1H, d, J=6 Hz, C$_6$—H) 7.40–7.10 (8H, m, Ar—H) 6.37–6.18 (1H, m, C$_{1'}$—H) 3.63 (1H broad s, OH) 2.58–1.82 (2H, m, C$_{2'}$—H).

The following Examples 8 to 20 were conducted in the same manner as in Example 7 to give the compounds in a glassy form mentioned below.

EXAMPLE 8

Di-o-chlorophenyl 2'-deoxy-5-fluoro-5'-uridylate

Yield 18%.

$^1$H—NMR (CDCl$_3$) δ (ppm) 9.95 (1H, broad s, N$_3$—H) 7.60 (1H, d, J=6 Hz, C$_6$—H) 7.50–7.03 (8H, m, Ar—H) 6.33–6.19 (1H, m, C$_{1'}$—H) 4.68–4.43 (3H, m, C$_{3',5'}$—H) 4.23–4.10 (1H, m, C$_{4'}$—H) 3.72 (1H, broad s, OH) 2.53–1.80 (2H, m, C$_{2'}$—H).

EXAMPLE 9

Di-m-chlorophenyl 2'-deoxy-5-fluoro-5'-uridylate

Yield 15%.

$^1$H—NMR (CDCl$_3$) δ (ppm) 0.12 (1H, broad s, N$_3$—H) 7.50 (1H, d, J=6 Hz, C$_6$—H) 7.30–6.93 (8H, m, Ar—H) 6.27–6.07 (1H, m, C$_{1'}$—H) 4.53–4.27 (3H, m, C$_{3',5'}$—H) 4.15–4.00 (1H, m, C$_{4'}$—H) 3.90 (1H, broad s, OH) 2.47–1.73 (2H, m, C$_{2'}$—H).

EXAMPLE 10

Di(2,3-dichlorophenyl) 2'-deoxy-5-fluoro-5'-uridylate

Yield 32%.

$^1$H—NMR (CDCl$_3$) δ (ppm) 0.43 (1H, broad s, N$_3$—H) 7.64 (1H, d, J=6 Hz, C$_6$—H) 7.45–7.00 (6H, m, Ar—H) 6.36–6.20 (1H, m, C$_{1'}$—H) 4.73–4.43 (3H, m, C$_{3',5'}$—H) 4.30–4.13 (1H, m, C$_{4'}$—H) 4.00 (1H, broad s, OH) 2.60–1.83 (2H, m, C$_{2'}$—H).

EXAMPLE 11

Di(2,4-dichlorophenyl) 2'-deoxy-5-fluoro-5 -uridylate

Yield 30%.

$^1$H—NMR (CDCl$_3$) δ (ppm) 7.60 (1H, d, J=6 Hz, C$_6$—H) 7.48–6.86 (6H, m, Ar—H) 6.30–6.17 (1H, m, C$_{1'}$—H) 4.67–4.42 (3H, m, C$_{3',5'}$—H) 4.25–4.12 (1H, m, C$_{4'}$—H) 2.55–1.88 (2H, m, C$_{2'}$—H).

EXAMPLE 12

Di(3,4-dichlorophenyl) 2'-deoxy-5-fluoro-5'-uridylate

Yield 16%.

$^1$H—NMR (CDCl$_3$) δ (ppm) 9.58 (1H, broad s, N$_3$—H) 7.58 (1H, d, J=6 Hz, C$_6$—H) 7.51–7.04 (6H, m, Ar—H) 6.31–6.04 (1H, m, C$_{1'}$—H) 60–4.40 (3H, m, C$_{3',5'}$—H) 4.25–4.10 (1H, m, C$_{4'}$—H) 3.20 (1H, broad s, OH) 2.53–1.83 (2H, m, C$_{2'}$—H).

EXAMPLE 13

Di(3,4-methylenedioxyphenyl) 2'-deoxy-5-fluoro-5'-uridylate

Yield 54%.

$^1$H—NMR (CDCl$_3$) δ (ppm) 7.59 (1H, d, J=6 Hz, C$_6$—H) 6.77–6.63 (6H, m, Ar—H) 6.33–6.03 (1H, m, C$_{1'}$—H) 5.98 (4H, s, O—CH$_2$—O) 4.57–4.37 (3H, m, C$_{3',5'}$—H) 4.20–4.03 (1H, m, C$_{4'}$—H) 2.54–1.77 (2H, m, C$_{2'}$—H).

EXAMPLE 14

Di-p-methoxyphenyl 2'-deoxy-5-fluoro-5'-uridylate

Yield 65%.

$^1$H—NMR (CDCl$_3$) 7.60 (1H, d, J=6 Hz, C$_6$—H) 7.16, 6.86 (8H, d, d, J=7, 10 Hz, Ar—H) 6.33–6.18 (1H, m, C$_{1'}$—H) 4.53–4.40 (3H, m, C$_{3',5'}$—H) 4.17–4.07 (1H, m, C$_{4'}$—H) 3.78 (6H, s, OCH$_3$) 2.50–1.80 (2H, m, C$_{2'}$—H).

EXAMPLE 15

Di-p-methylthiophenyl 2'-deoxy-5-fluoro-5'-uridylate

Yield 14%.

$^1$H—NMR (CDCl$_3$) δ (ppm) 9.67 (1H, broad s, N$_3$—H) 7.52 (1H, d, J=6 Hz, C$_6$—H) 7.16–7.00 (8H, m, Ar—H) 6.23–6.08 (1H, m, C$_{1'}$—H) 4.50–4.30 (3H, m, C$_{3',5'}$—H) 4.13–4.00 (1H, m, C$_{4'}$—H) 3.52 (1H, broad s, OH) 2.40 (6H, s, SCH$_3$) 2.60–1.57 (2H, m, C$_{2'}$—H).

EXAMPLE 16

Di-p-cyanophenyl 2'-deoxy-5-fluoro-5'-uridylate

Yield 54%.

$^1$H—NMR (CDCl$_3$—MeOH—d$_6$) δ (ppm) 7.73, 7.37 (8H, d, d, J=9, 10 Hz, Ar—H) 7.57 (1H, d, J=6 Hz, C$_6$—H) 6.30–6.12 (1H, m, C$_{1'}$—H) 4.60–4.26 (3H, m, C$_{3',5'}$—H) 4.15–4.03 (1H, m, C$_{4'}$—H) 2.52–1.58 (2H, m, C$_{2'}$—H).

EXAMPLE 17

Di-p-fluorophenyl 2'-deoxy-5-fluoro-5'-uridylate

Yield 18%.

$^1$H—NMR (Me$_2$SO—d$_6$) δ (ppm) 7.47 (1H, d, J=6 Hz, C$_6$—H) 7.28, 7.20 (8H, s, s, Ar—H) 6.20–6.00 (1H, m, C$_{1'}$—H) 4.50–4.28 (2H, m, C$_{5'}$—H) 4.23–4.01 (1H, m, C$_{4'}$—H) 4.00–3.78 (1H, m, C$_{3'}$—H) 2.20–2.00 (2H, m, C$_{2'}$—H).

EXAMPLE 18

Di-p-bromophenyl 2'-deoxy-5-fluoro-5'-uridylate

Yield 8%.

$^1$H—NMR (CDCl$_3$) δ (ppm)
7.56 (1H, d, J=6 Hz, C$_6$—H) 7.45, 7.06 (8H, d, d, J=9, 11 Hz, Ar—H) 6.27–6.10 (1H, m, C$_{1'}$—H) 4.56–4.30 (3H, m, C$_{3',5'}$—H) 4.19–4.19 (1H, m, C$_{4'}$—H) 2.53–1.77 (2H, m, C$_{2'}$—H).

EXAMPLE 19

Di-p-trifluoromethylphenyl 2'-deoxy-5-fluoro-5'-uridylate

Yield 10%.

$^1$H—NMR (CDCl$_3$) δ (ppm) 7.65–7.25 (9H, m, C$_6$—H, Ar—H) 6.27–6.12 (1H, m, C$_{1'}$—H) 4.60–4.37

(3H, m, $C_{3',5'}$—H) 4.21–4.05 (1H, m, $C_{4'}$—H) 2.53–1.83 (2H, m, $C_{2'}$—H).

EXAMPLE 20

Di-1-naphthyl 2'-deoxy-5-fluoro-5'-uridylate

Yield 52%.

$^1$H—NMR (CDCl$_3$) δ (ppm) 8.10–7.20 (15H, m, $C_6$—H, Ar—H) 6.13–5.93 (1H, m, $C_{1'}$—H) 4.55–4.33 (2H, m, $C_{5'}$—H) 4.30–4.09 (1H, m, $C_{4'}$—H) 4.09–3.92 (1H, m, $C_{3'}$—H) 2.23–1.67 (2H, m, $C_{2'}$—H).

EXAMPLE 21

Di-4-methoxycarbonylphenyl 2'-deoxy-5-fluoro-5'-uridylate

Yield 48%.

$^1$H—NMR (CDCl$_3$) δ (ppm) 8.15, 7.29 (8H, d, d, J=9,9 Hz, Ar—H) 7.53 (1H, d, J=6 Hz, $C_6$—H) 6.30–6.17 (1H, m, $C_{1'}$—H) 4.62–4.40 (3H, m, $C_{3',5'}$—H) 4.25–4.12 (1H, m, $C_{4'}$—H) 3.92 (6H, s, OCH$_3$) 2.55–1.90 (2H, m, $C_{2'}$—H).

EXAMPLE 22

Production of di-p-chlorophenyl 3'-acetyl-2'-deoxy-5-fluoro-5'-uridylate

In 5 ml of pyridine was dissolved 300 mg (1.04 mmol) of 3'-acetyl-2'-deoxy-5-fluorouridine. To the solution was added 500 mg (1.48 mmol) of di-p-chlorophenyl-phosphorochloridate as obtained by the same method as in Example 7, and the mixture was stirred at room temperature overnight. To the reaction mixture was added 50 ml of toluene, and the solvent was distilled off under reduced pressure. To the obtained residue was again added 50 ml of toluene, and the solvent was distilled off under reduced pressure. The obtained residue was purified by preparative liquid chromatography (LC-09 type, Manufactured by Japan Analysis Ind. Ltd., Column: JAIGEL-1H, Solvent: chloroform) to give 247 mg of di-p-chlorophenyl 3'-acetyl-2'-deoxy-5-fluoro-5'-uridylate in a glassy form (Yield 40%).

$^1$H—NMR (CDCl$_3$) δ (ppm) 9.17 (1H, broad s, N$_3$—H) 7.67 (1H, d, J=6 Hz, $C_6$—H) 7.43–7.13 (8H, m, Ar—H) 6.40–6.23 (1H, m, $C_{1'}$—H) 5.30–5.20 (1H, m, $C_{3'}$—H) 4.61–4.50 (2H, m, $C_{5'}$—H) 4.27–4.17 (1H, m, $C_{4'}$—H) 2.13 (3H, s, CH$_3$) 2.60–1.83 (2H, m, $C_{2'}$—H).

EXAMPLE 23

Production of dibenzyl 2'-deoxy-5-fluoro-5'-uridylate

In 2 ml of tetrahydrofuran were dissolved 400 mg (1.62 mmol) of 2'-deoxy-5-fluorouridine, 662 mg (2.38 mmol) of dibenzyl phosphate and 654 mg (2.49 mmol) of triphenylphosphine. To this solution was added a solution of 424 mg (2.43 mmol) of diethylazodicarboxylate in 2 ml of tetrahydrofuran, and the mixture was stirred at room temperature overnight. The solvent was distilled off under reduced pressure, and ethyl acetate was added to the residue. The resulting triphenylphosphineoxide was filtered off. The filtrate was concentrated under reduced pressure. The obtained concentrate was subjected to silica gel column chromatography with the use of ethyl acetate as the eluent to give 337 mg of dibenzyl 2'-deoxy-5-fluoro-5'-uridylate in a glassy form (Yield 46%).

$^1$H—NMR (CDCl$_3$) δ (ppm) 7.67 (1H, d, J=6 Hz, $C_6$—H) 7.43–7.32 (10H, m, Ar—H) 6.35–6.17 (1H, m, $C_{1'}$—H) 5.08 (4H, d, J=9 Hz, Ph—CH$_2$) 4.50–4.00 (4H, m, $C_{3',4',5'}$—H) 2.55–1.77 (2H, m, $C_{2'}$—H).

EXAMPLE 24

Production of di-p nitrophenyl 2'-deoxy-5-fluoro-5'-uridylate

A solution of 600 mg (2.44 mmol) of 2'-deoxy-5-fluorouridine in 6 ml of pyridine was cooled to −10° C. to 0° C. in an ice-water bath. To this solution was added dropwise a mixture of 1.50 g (4.95 mmol) of 2,4,6-triisopropylbenzenesulfonylchloride, 830 mg (2.44 mmol) of bis(4-nitrophenyl)phosphate and 25 ml of pyridine over the period of 30 minutes. After the completion of the dropwise addition, the mixture was stirred at room temperature overnight. The solvent was distilled off under reduced pressure. The residue was subjected to silica gel column chromatography with the use of a mixture of chloroform and methanol (9:1 v/v) as the eluent to give 510 mg of di-p-nitrophenyl 2'-deoxy-5-fluoro-5'-uridylate in a glassy form (Yield 37%).

$^1$H—NMR (CD$_3$OD) δ (ppm) 8.34, 7.52 (8H, d, d, J=9, 10 Hz, Ar—H) 7.71 (1H, d, J=6 Hz, $C_6$—H) 6.27–6.12 (1H, m, $C_{1'}$—H) 4.67–4.00 (4H, m, $C_{3',4',5'}$—H) 2.32–2.17 (2H, m, $C_{2'}$—H).

EXAMPLE 25

Production of 2'-deoxy-5-fluorouridine 5'-(S,S-diphenylphosphorodithioate) [The compound of the formula (I) wherein R$^1$, R$^3$=H, R$^2$=(PhS)$_2$P(=O)—, Ph representing phenyl group]

A solution of 500 mg (2.03 mmol) of 2'-deoxy-5-fluorouridine in 5 ml of pyridine was cooled to −10° C. to 0° C. in an ice-water bath. To this solution was added dropwise a mixture of 1.00 g (3.30 mmol) of 2,4,6-triisopropylbenzenesulfonylchloride, 1.36 g (3.56 mmol) of S,S-diphenylphosphorodithioate monocyclohexylammonium and 5 ml of pyridine over the period of 10 minutes. After the completion of the dropwise addition, the mixture was stirred at room temperature overnight. To this reaction mixture was added 100 ml of water. The mixture was extracted with 10 ml of chloroform repeatedly three times. The extract was washed with an aqueous solution of dilute hydrochloric acid and water in order, and then dried over anhydrous magnesium sulfate. The solvent was distilled off under reduced pressure The obtained residue was subjected to silica gel column chromatography with the use of a mixture of chloroform and methanol (9:1 v/v) as the eluent to give 599 mg of 2'-deoxy-5-fluorouridine 5'-(S,S-diphenylphosphorodithioate) in a glassy form (Yield 55%).

$^1$H—NMR (CDCl$_3$) δ (ppm) 7.63–7.27 (11H, m, $C_6$—H, Ar—H) 6.35–6.17 (1H, m, $C_{1'}$—H) 4.56–4.28 (3H, m, $C_{3',5'}$—H) 4.17–4.05 (1H, m, $C_{4'}$—H) 2.52–1.77 (2H, m, $C_{2'}$—H).

EXAMPLE 26

Production of 2'-deoxy-5-fluorouridine 5'-(S,S-di-p-chlorophenylphosphorodithioate) [The compound of the formula (I) wherein R$^1$,R$^3$=H, R$^2$=(p—Cl—PhS)$_2$ P(=O), P—Cl—Ph representing p-chlorophenyl group]

By the same method as in Example 25 was obtained 2'-deoxy-5-fluorouridine 5'-(S,S-di-p-chlorophenyl-phosphorodithioate) in a glassy form (Yield 30%).

$^1$H NMR (CDCl$_3$—CD$_3$OD) δ (ppm) 7.60–7.30 (9H, m, $C_6$—H, Ar—H) 6.30–6.15 (1H, m, $C_{1'}$—H) 4.50–4.20

(4H, m, $C_{3',4',5'}$—H) 2.43–1.83 (2H, m, $C_{2'}$—H) tumour composition.

Given below are Preparation Examples illustrating the preparation of pharmaceutical compositions containing the compound of the invention.

PREPARATION EXAMPLE 1

Preparation of encapsulated composition

The compound obtained in Example 7, lactose, crystalline cellulose and corn starch were mixed together in the following proportions. Magnesium stearate was added in the amount shown below, and the mixture was encapsulated in an amount of about 300 mg per capsule with the use of a suitable encapsulating device.

| Components | mg/capsule |
|---|---|
| Compound obtained in Example 7 | 200.0 |
| Lactose | 30.0 |
| Crystalline cellulose | 50.0 |
| Corn starch | 17.0 |
| Magnesium stearate | 3.0 |
|  | 300.0 |

PREPARATION EXAMPLE 2

Preparation of granulated composition

The compound obtained in Example 17, lactose, crystalline celulose and corn starch were mixed together in the following proportions. A 10% solution of hydroxypropyl cellulose in ethanol was added and the mixture was kneaded and granulated with the use of an adequate granulation device. The granules were dried and regulated to a size of 12 to 42 meshes. The resulting granules were coated with hydroxypropylmethyl cellulose in the amount shown below with the use of a suitable coater and regulated to a size of 12 to 42 meshes.

| Components | mg/capsule |
|---|---|
| Compound obtained in Example 17 | 200.0 |
| Lactose | 200.0 |
| Crystalline cellulose | 311.0 |
| Corn starch | 200.0 |
| Hydroxypropyl cellulose | 10.0 |
| Hydroxypropylmethyl cellulose | 70.0 |
| Fatty acid monoglyceride | 3.5 |
| Titanium dioxide | 5.5 |
|  | 1,000.0 |

PREPARATION EXAMPLE 3

Preparation of composition in suppository form

"Witepsol W-35" (trademark, product of Dynamite Nobel Co., Ltd., West Germany) was fused at about 60° C. and the solution was maintained at about 45° C. The solution and the compound obtained in Example 19 was mixed in the following proportions and shaped into a suppository form weighing 1 g each with the use of a suitable suppository-forming device.

| Components | mg/suppository |
|---|---|
| Compound obtained in Example 19 | 400.0 |
| Witepsol W-35 | 600.0 |
|  | 1,000.0 |

PREPARATION EXAMPLE 4

| Compound obtained in Example 7 | 10 mg |
|---|---|
| Macrogol 300 | 500 mg |

An injection solution (5 ml per ampoule) was prepared which had the foregoing composition.

We claim:

1. A 2'-deoxy-5-fluorouridine derivative of the formula

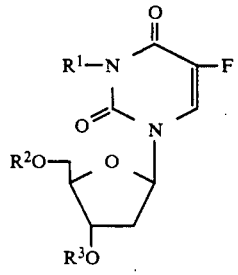

wherein, $R^1$ is hydrogen atom or an acyl group and $R^2$ and $R^3$ are respectively hydrogen atom, an acyl group or a group of the formula

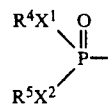

wherein $X^1$ and $X^2$ are respectively oxygen atom or sulfur atom; $R^4$ is a phenyl group, a benzyl group or a naphthyl group each of which may be substituted by an alkyl group, an alkoxyl group, an alkoxycarbonyl group, an alkylthio group, an acyl group, a halogen atom, trifluoromethyl group, nitro group, cyano group, carboxyl group and/or methylenedioxy group and $R^5$ is an alkyl group, an alkenyl group or one of the groups represented by $R^4$ which is the same as or different from $R^4$, at least one of $R^2$ and $R^3$ being a group of the formula

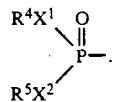

2. The 2'-deoxy-5-fluorouridine derivative as claimed in claim 1 wherein $R^2$ is a group of the formula

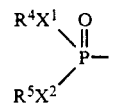

wherein the symbols are as defined in claim 1.

3. The 2'-deoxy-5-fluorouridine derivative as claimed in claim 1 wherein $R^1$ and $R^3$ are respectively hydrogen atom or an acyl group.

4. The 2'-deoxy-5-fluorouridine derivative as claimed in claim 1 wherein $R^2$ is a group of the formula

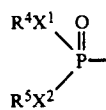

wherein each of $X^1$ and $X^2$ is oxygen atom and $R^4$ and $R^5$ are respectively a phenyl group substituted by one or two chlorine atom, fluorine atom, bromine atom and/or trifluoromethyl group.

5. The 2'-deoxy-5-fluorouridine derivative as claimed in claim 1, wherein $R^1$ is a hydrogen atom; $R^2$ is a group of the formula

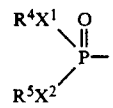

wherein each of $X^1$ and $X^2$ is oxygen atom and $R^4$ and $R^5$ are respectively a phenyl group substituted by one or two chlorine atom, fluorine atom, bromine atom and/or trifluoromethyl group; $R^3$ is hydrogen atom or an acyl group.

6. The 2'-deoxy-5-fluorouridine derivative as claimed in claim 1 selected from the group consisting of di-p-chlorophenyl 2'-deoxy-5-fluoro-5'-uridylate, di-m-chlorophenyl 2'-deoxy-5-fluoro-5'-uridylate, di(2,4-dichlorophenyl) 2'-deoxy-5-fluoro-5'-uridylate, di-p-fluorophenyl 2'-deoxy-5-fluoro-5'-uridylate, di-p-bromophenyl 2'-deoxy-5-fluoro-5'-uridylate, de-p-trifluoromethylphenyl 2'-deoxy-5-fluoro-5'-uridylate and di-p-chlorophenyl 3'-acetyl-2'-deoxy-5-fluoro-5'-uridylate.

7. A composition comprising an amount of a 2'-deoxy-5-fluorouridine derivative, as claimed in claim 1, effective to treat Sarcoma 180 tumor cells transplanted to mice, and a pharmaceutically acceptable carrier.

* * * * *